United States Patent [19]

Persson et al.

[11] Patent Number: 5,866,557
[45] Date of Patent: Feb. 2, 1999

[54] USE OF AN ESTER OF INOSITOLTRISPHOSPHATE FOR THE TREATMENT OF INFLAMMATORY CONDITIONS

[75] Inventors: Lars Persson, Hassleholm; Nicola Rehnberg; Torgny Gustafsson, both of Perstorp, all of Sweden

[73] Assignee: Perstorp AB, Sweden

[21] Appl. No.: 640,785

[22] PCT Filed: Nov. 18, 1994

[86] PCT No.: PCT/SE94/01095

§ 371 Date: Jul. 22, 1996

§ 102(e) Date: Jul. 22, 1996

[87] PCT Pub. No.: WO95/14477

PCT Pub. Date: Jun. 1, 1995

[30] Foreign Application Priority Data

Nov. 22, 1993 [SE] Sweden .................................. 9303854

[51] Int. Cl.$^6$ ...................................................... A61K 31/66
[52] U.S. Cl. ............................................................ 514/102
[58] Field of Search ............................................. 514/102

[56] References Cited

U.S. PATENT DOCUMENTS 4,515,722  5/1985  Yang et al. .

FOREIGN PATENT DOCUMENTS

| 179 439 | 4/1986 | European Pat. Off. . |
| 269 105 | 6/1988 | European Pat. Off. . |
| 359 256 | 3/1990 | European Pat. Off. . |
| 420 428 | 4/1991 | European Pat. Off. . |
| WO 91/09601 | 7/1991 | WIPO . |

OTHER PUBLICATIONS

P.B. Curtis–Prior, "Prostaglandins, an Introduction to Their Biochemistry, Physiology and Pharmacology," (1976) North–Holland Publishing Company, p. 43.

*Primary Examiner*—Zohreh Fay
*Attorney, Agent, or Firm*—Scully, Scott, Murphy & Presser

[57] ABSTRACT

The present invention relates to the use of an ester of inositoltrisphosphate for the preparation of a medicament for preventing, alleviating or combatting inflammatory conditions in mammals including man.

Injury or destruction of tissues should be understood as damage to an aggregation of specialized cells with a particular function both internally and externally in the body, such as different organs or parts of these, vessels, skin etc.

Tissue damage involves a complex series of events such as dilatation of vessel walls e.g. arterioles, capillaries and venules, increased permeability of fluids including e.g. plasma proteins and increased blood flow. Increased vascular leakage often results in extravasation and oedema formation which characterize the damage of different tissues.

Often tissue damage and inflammatory conditions are characterized by signs of pain, heat, redness, swelling and loss of function.

Tissue damage is not defined as a disease per se but is often a component in different diseases of both acute or chronic nature.

24 Claims, No Drawings

USE OF AN ESTER OF INOSITOLTRISPHOSPHATE FOR THE TREATMENT OF INFLAMMATORY CONDITIONS

Damage of tissues can be induced in many ways. Inducing factors can be correlated with mechanical effects, immunological effects or chemical effects. Microorganisms such as virus, bacteria and fungus can induce tissue damage and exposure to heat, fire, radiation, cold and blows most often results in such damage. Many diseases like asthma, eczema, psoriasis, rheumatoid arthritis, diabetes and arteriosclerosis also involve different types of tissue damage.

The existing treatments of diseases connected to tissue damage and inflammatory conditions are based on drugs such as non steroid antiinflammatory drugs (NSAID), steroids, antibiotics and cytostatics. In some cases also surgical therapy is used.

Existing drugs often suffer from limited effectiveness in combination with serious side effects. Toxic effects appearing from the treatment with NSAID:s can consist of gastrointestinal side effects, allergic reactions and side effects in the central nervous system. Treatment with steroids often results in side effects such as osteoporosis and fractures, increased susceptibility to infections and peptic ulcerations.

According to the present invention it has surprisingly become possible to overcome and reduce the above mentioned injuries and destructions of tissues by the use of an ester of inositoltrisphosphate for the preparation of a medicament for preventing, alleviating or combatting inflammatory conditions in mammals including man.

The invention also covers the use of an ester of inositoltrisphosphate for the preparation of a medicament for preventing, alleviating or combatting tissue damage in mammals including man.

In preferred embodiments of the invention the medicament is intended to be used for preventing, alleviating or combatting tissue damage related to oedema formation and vascular leakage. In other preferred embodiments of the invention the medicament is intended to be used for preventing, alleviating or combatting tissue damage related to burns, rhinitis, asthma and arthritis.

The invention relates to the use of an ester of inositoltrisphosphate for preparing a medicament for preventing, alleviating or combatting for example the following conditions:

Tissue damage and inflammatory conditions induced mechanically by heat and fire such as burns of first, second or third degree, trauma i.e. wounds or injuries caused by physical damage, or cold;

Tissue damage and inflammatory conditions induced chemically or by microorganisms such as radiation, sepsis and injuries caused by e.g. bee-stings, snake-bites etc;

Tissue damage and inflammatory conditions in diseases where the immunological component is strongly expressed such as rhinitis, hayfever, asthma, psoriasis, vasculitis and eczema. Furthermore the invention relates to treatment of tissue damage and inflammatory conditions related to erythema, herpes and arthritis, injuries caused by or following surgery and operations of grafts, catheters etc. and injuries caused by or occurring in the border zone of an infarct of cardiac type, cerebral type or any other type.

Other injuries of tissues related to diseases such as uveitis, otitis, stomatitis, peritonitis, sinusitis, gastroenteritis, colitis and cystitis are also related to the invention.

The medicament is effective against tissue damage connected to the above mentioned conditions but also to other conditions where tissue damage and inflammations occurs.

From the European Patent No 179439 a pharmaceutical composition comprising as a pharmaceutically active ingredient at least one isomer of inositoltrisphosphate is known. In said patent the effect of this pharmaceutical composition is shown for different areas, such as platelet aggregation.

The production of esters of inositoltrisphosphate and the isolation of the different isomers thereof are disclosed in the European Patent Application No 0269105.

The therapeutic profile of esters of inositoltrisphosphates differs from the profile of inositoltrisphosphates in many important aspects. Chemical properties such as lipophilicity, solubility and $pK_A$-values are changed which affect the potency and selectivity of the compound.

Furthermore the susceptibility against enzymatic degradation is markedly lowered for esters of inositoltrisphosphates which result in a prolonged duration.

It is suitable that the medicament used according to the invention exists in unit dosage form. Tablets, granules or capsules are suitable administration forms for such unit dosage. Furthermore, tablets and granules can easily be surface treated such as to provide an enteric coating to prevent an uncontrolled hydrolysis in the stomach and to bring about a desired absorption in the intestine. Other suitable administration forms are slow release and transdermal administration. A usual pharmaceutically acceptable additive, excipient and/or carrier can be included in the medicament. The tablets or granules can also contain a disintegrant which causes the tablets or the granules, respectively, to disintegrate easily in the intestine. In certain cases, especially in acute situations, it is preferable to use the unit dosage in the form of a solution for intravenous administration. In other situations suspensions comprising the compound can be preferably used as administration form.

The medicament can also consist as such of esters of inositoltrisphosphate solely without any additive, excipient or carrier.

The medicament can consist of or comprise one or more specific isomers of esters of inositoltrisphosphate each present in substantialy pure form. Thus, the different isomers can be isolated from each other in substantially pure form, which means that they have a purity of 80–100%, such as 82–100% or 85–100%, preferably 90–100%. Since the isomers can be produced in pure form they can be mixed in any proportion, of course.

It is in most cases suitable that the ester of inositoltrisphosphate used for the preparation of the medicament according to the invention are present in salt form in order not to affect the mineral balance negatively. The salt should preferably consist of a sodium, potassium, calcium zinc or magnesium salt or a mixture of two or more of these salts.

For the above mentioned reasons it is also an advantage if the medicament contains a surplus or an extra addition of at least one pharmaceutically acceptable salt of calcium, zinc or magnesium with a mineral acid or organic acid. This is especially valuable for elderly persons who are often deficient in these minerals.

For administration to human patients appropriate dosages can routinely be determined by those skilled in this art by extension of the results obtained in animals at various dosages. The preferred dosage for humans falls within the range of 0,1 to 1000 mg, especially 0.1–200 mg of the compound/day/kg body weight.

In animal experiments, no toxic effects were seen after administration of very high doses of esters of inositoltrisphosphates, 300 mg/kg body weight by intravenous injection to mice.

The medicament usually contains 0.01–1.5 g, such as 0.05–1.3 g or preferably 0.1–1 g of the compound per unit dosage.

The composition used according to the present invention contains at least one, sometimes two or more of the following compounds, which correspond to esters of inositoltrisphosphates with the structural formula:

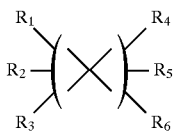

where $R_1$, $R_2$ and $R_3$ are vicinal and all are

where A is
(1) straight or branched chain alkyl containing 1 to 24 carbon atoms
(2) cycloalkyl containing 3 to 16 carbon atoms
(3) alkenyl containing 2 to 24 carbon atoms
(4) cycloalkenyl containing 5 to 16 carbon atoms
(5) aryl containing 6 to 24 carbon atoms
(6) aralkyl containing 7 to 48 carbon atoms
(7) alkaryl containing 7 to 48 carbon atoms
(8) aralkenyl containing 8 to 48 carbon atoms
(9) alkenylaryl containing 8 to 48 carbon atoms
(10) a heterocyclic ring containing at least one atom of oxygen, nitrogen or sulfur said meanings (1) to (10) being unsubstituted or substituted with hydroxy, oxo, alkoxy, aryloxy, halo, cyano, isocyano, carboxy, esterified carboxy, amino, substituted amino, formyl, acyl, acyloxy, acylamino, sulfinyl, sulfonyl, phosphine, phosphinyl, phosphonyl, mercapto, alkylthio, arylthio, silyl, silyloxy, silylthio, nitro or azido
(11) carboxy
(12) esterified carboxy
(13) amino or
(14) substituted amino where $R_4$, $R_5$ and $R_6$ are vicinal and all are

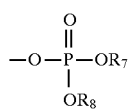

where $R_7$ and $R_8$ are the same or different and are
(1) hydrogen
(2) mono-, di- or trivalent cation and where X is a radical of myo-inositol or a configuration isomer thereof.

The substituent A could be the same for all $R_1$, $R_2$ and $R_3$ or could have different structures following the above definition.

In another preferred embodiment of the invention $R_1$, $R_2$ and $R_3$ are vicinal and all are (1)

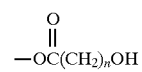

where n is an integer between 1 and 10; preferably n is between 2 and 4

(2)

where n is an integer between 1 and 10 and where $R_9$ is a substituted or unsubstituted straight or branched alkyl, cycloalkyl, aryl or alkaryl; preferably n is between 2 and 4 and $R_9$ is a lower alkyl such as methyl, ethyl or propyl.

(3)

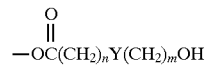

where n and m is an integer between 1 and 10 and where Y is oxygen or sulphur; preferably n is 1 and m is between 2 and 4.

(4)

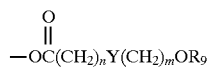

where n and m is an integer between 1 and 10, where Y is oxygen or sulphur and where $R_9$ is a substituted or unsubstituted straight or branched alkyl, cycloalkyl, aryl or alkaryl; preferably n is 1, m is between 2 and 4 and $R_9$ is a lower alkyl such as methyl, ethyl or propyl.

(5)

where n is an integer between 1 and 10 and where $R_9$ is a substituted or unsubstituted, straight or branched alkyl, cycloalkyl, aryl or aralkyl; preferably n is 1 or 2 and $R_9$ is a lower alkyl such as methyl, ethyl or propyl.

(6)

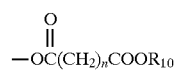

where n is an integer between 1 and 10 and where $R_{10}$ is hydrogen or a substituted or unsubstituted, straight or branched alkyl, cycloalkyl, aryl or aralkyl; preferably n is 2 or 3 and $R_{10}$ is hydrogen or a lower alkyl such as methyl, ethyl or propyl.

(7)

where n is an integer between 1 and 10 and where $R_9$ is a substituted or unsubstituted, straight or branched alkyl, cycloalkyl, aryl or aralkyl; preferably n is 1 and $R_9$ is a lower alkyl such as methyl, ethyl or propyl.

(8)

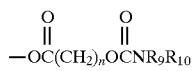

where n is an integer between 1 and 10 and where $R_9$ is a substituted or unsubstituted, straight or branched alkyl, cycloalkyl, aryl or aralkyl, and where $R_{10}$ is hydrogen or substituted or unsubstituted, straight or branched alkyl, cycloalkyl, aryl or aralkyl; preferably n is 1, $R_9$ is lower alkyl such as methyl, ethyl or propyl and $R_{10}$ is hydrogen.

(9)

where n is an integer between 1 and 10 and where $R_9$ is a substituted or unsubstituted, straight or branched alkyl, cycloalkyl, aryl or aralkyl and where $R_{10}$ is hydrogen or substituted or unsubstituted, straight or branched alkyl, cycloalkyl, aryl or aralkyl; preferably n is 1, $R_9$ is lower alkyl such as methyl, ethyl or propyl and $R_{10}$ is hydrogen.

(10)

where n is an integer between 1 and 10 and where $R_9$ is a substituted or unsubstituted, straight or branched alkyl, cycloalkyl, aryl or aralkyl; preferably n is 1 and $R_9$ is a lower alkyl such as methyl, ethyl or propyl.

(11)

where $Z^1$ is substituted or unsubstituted such as $CH(CH_2)_2$, $CH(CH_2)_3$, $CH(CH_2)_4$, $CH(CH_2)_5$, $CH(CH_2)_6$ or $CH(CH_2)_2(CH)_2$.

(12)

where $Z^1$ is substituted or unsubstituted cycloalkyl such as $CH(CH_2)_2$, $CH(CH_2)_3$, $CH(CH_2)_4$, $CH(CH_2)_5$, $CH(CH2)6$ or $CH(CH_2)_2(CH)_2$ and where n is an integer between 1 and 10; preferably n is 1.

(13)

where $Z^2$ is substituted or unsubstituted phenyl, biphenyl, naphtyl, anthracenyl or phenantrenyl.

(14)

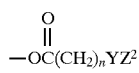

where $Z^2$ is substituted or unsubstituted phenyl, biphenyl, naphtyl, anthracenyl or phenantrenyl and where n is an integer between 1 and 10; preferably n is 1.

(15)

where $Z^3$ is substituted or unsubstituted heterocyclic compound such as

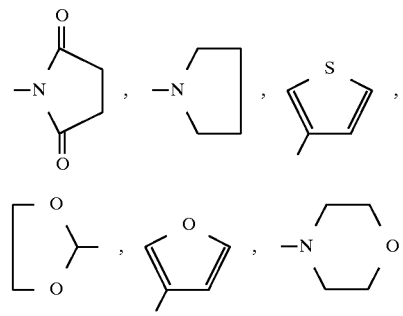

(16)

where $Z^3$ is substituted or unsubstituted heterocyclic compound such as

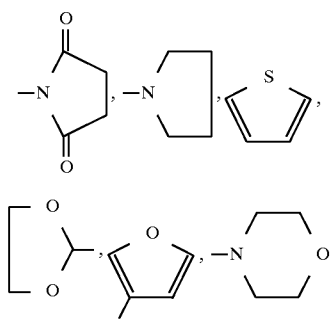

(17)

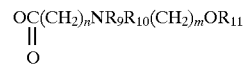

where n and m is an integer between 1 and 10, where $R_9$ is a substituted or unsubstituted, straight or branched alkyl, cycloalkyl, aryl, alkaryl and where $R_{10}$ and $R_{11}$ are hydrogen or substituted or unsubstituted straight or branched alkyl, cycloalkyl, aryl, alkaryl; preferably n is 1 or 2, m is 2 or 3, $R_9$ is lower alkyl and $R_{10}$ and $R_{11}$ are hydrogen.

(18) -O-acetyl, -O-propionyl, -O-butyryl, -O-isobutyryl, -O-(4-acetoxy)butyryl, -O-valeryl, -O-isovaleryl, -O-(4-propionyloxy)valeryl, -O-pivaloyl, -O-hexanoyl, -O-octanoyl, -O-decanoyl, -O-dodecanoyl, -O-tetradecanoyl, -O-hexadecanoyl or -O-octadecanoyl.

(19) -O-methylcarbamoyl, -O-ethylcarbomoyl, -O-propylcarbamoyl, -O-butylcarbamoyl, -O-phenylcarbamoyl, -O-benzoylcarbamoyl, -O-(2-acetoxy)benzoylcarbamoyl, -O-(2-propionyloxy) benzoylcarbamoyl or chlorosulfonylcarbamoyl.

The formula above discloses specific esters of inositol-trisphosphates where the inositol moiety is selected from the group of myoinositol, cisinositol, epiinositol, alloinositol, neoinositol, mucoinositol, chiroinositol and scylloinositol.

In one preferred embodiment of the invention the compound used in the preparation of a medicament effective against inflammatory conditions has the structural formula

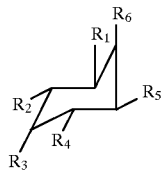

where $R_1$, $R_2$ and $R_3$ are vicinal and all are

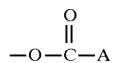

where A is
(1) straight or branced chain alkyl containing 1 to 24 carbon atoms
(2) cycloalkyl containing 3 to 16 carbon atoms
(3) alkenyl containing 2 to 24 carbon atoms
(4) cycloalkenyl containing 5 to 16 carbon atoms
(5) aryl containing 6 to 24 carbon atoms
(6) aralkyl containing 7 to 48 carbon atoms
(7) alkaryl containing 7 to 48 carbon atoms
(8) aralkenyl containing 8 to 48 carbon atoms
(9) alkenylaryl containing 8 to 48 carbon atoms
(10) a heterocyclic ring containing at least one atom of oxygen, nitrogen or sulfur said meanings (1) to (10) being unsubstituted or substituted with hydroxy, oxo, alkoxy, aryloxy, halo, cyano, isocyano, carboxy, esterified carboxy, amino, substituted amino, formyl, acyl, acyloxy, acylamino, sulfinyl, sulfonyl, phosphino, phosphinyl, phosphonyl, mercapto, alkylthio, arylthio, silyl, silyloxy, silylthio, nitro or azido
(11) carboxy
(12) esterfied carboxy
(13) amino or
(14) substituted amino
and where $R_4$, $R_5$ and $R_6$ all are

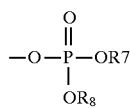

where $R_7$ and $R_8$ are the same or different and are
(1) hydrogen or
(2) mono, di- or trivalent cation.

The compounds contemplated in this embodiment of the invention are esters of myo-inositoltrisphosphates and preferred compounds are esters of D-myo-inositol-1,2,6-trisphosphates.

The invention will be further explained in the following examples where Example 1 shows the manufacturing of a solution of an ester of myo-inositoltrisphosphate for intravenous administration and Example 2–6 demonstrate the manufacture of different esters of myo-inositoltrisphosphate and Example 7 and 8 illustrate the inhibiting effect of esters of myo-inositoltrisphosphate against inflammation.

EXAMPLE 1

Solution of the sodium salt of D-3,4,5-tri-O-hexanyl-myo-inositol-1,2,6-trisphosphate (PP 10-202) for injection.

0.5 g of the sodium salt of PP 10-202 and 0.77 g sodium chloride were dissolved in 98.73 ml of water for injection to form a solution suitable for injection into a person or an animal.

EXAMPLE 2

1.92 mmol of the acid form of D-myo-inositol-1,2,6-trisphosphate ($IP_3$) was evaporated for the elimination of any residue of water and was then dissolved in 25 ml dimethylformamide (DMF). 1.24 g triethylamine was added followed by evaporation and an addition of 1.15 g 4-dimethylamino pyridine. To this solution, 5.30 g 4-acetoxybutyric anhydride dissolved in 10 ml dimethylene chloride was added during 30 minutes. The reaction mixture was stirred for 3 hrs at room temperature and then evaporated to dryness.

The residue was dissolved in 10 ml methanol and was extracted with 3×20 ml of heptane. The methanol-fraction was evaporated and the remaining product was analysed with NMR. Structural determination and NMR showed the compound to be D-3,4,5-tri-O-(4-acetoxybutyryl)-myo-inositol-1,2,6-trisphosphate.

EXAMPLE 3

In experiments similar to the procedure described in example 2 the following esters of D-myo-inositol-1,2,6-trisphosphate were synthesized in good yield:
D-3,4,5-tri-O-propionyl-myo-inositol-1,2,6-trisphosphate
D-3,4,5-tri-O-butyryl-myo-inositol-1,2,6-trisphosphate
D-3,4,5-tri-O-isobutyryl-myo-inositol-1,2,6-trisphosphate
D-3,4,5-tri-O-4-hydroxypentanoyl-myo-inositol-1,2,6-trisphosphate
D-3,4,5-tri-O-dodecanoyl-myo-inositol-1,2,6-trisphosphate.

EXAMPLE 4

1.4 g of D-myo-inositol-1,2,6-tris(N-ethyldiisopropyl ammonium hydrogen phosphate) was dissolved in 15 ml methylene chloride. 1.59 g hexanoic anhydride, 1.4 ml N-ethyldiisopropyl amine and 403 mg 4-(dimethylamino) pyride was added and the reaction mixture was stirred for 16 hrs at 40° C. The solvent was removed by evaporation and to the residue was added 15 ml tetrahydrofuran and 20 ml water.

The resulting suspension was purified by ion exchange chromatography (Dowex 50 W-X8) with water as eluent. The eluate was neutralized with sodium hydrogen carbonate and the water was removed. The residue was identified with NMR to be D-3,4,5-tri-O-hexanoyl-myo-inositol-1,2,6-trisphosphate.

EXAMPLE 5

5 g of the N-ethyldiisopropylamine salt of D-myo-inositol-1,2,6-trisphosphate was dissolved in 10 ml dimethylene chloride. 1.44 g 4-(dimethylamino)pyridine and 5 ml ethyldiisopropyl amine was added followed by dropwise addition of 5.75 ml phenylisocyanate during 60 minutes. The reaction mixture was stirred for 6 hours at room temperature and was then evaporated to dryness. The residue was dissolved in 30 ml tetrahydrofuran and 6 ml water followed by treatment with a cation exchange resin in $H^+$-form. The product was eluated with 200 ml of water and was treated with sodium hydrogen carbonate to reach pH 5.8. After filtration the supernatant was evaporated to dryness and analysed with NMR. The compound was identified as D-3,4,5-tri-O-phenylcarbamoyl-myo-inositol-1,2,6-trisphosphate.

EXAMPLE 6

In experiments similar to the procedure described in example 5 the following carbamates of D-myo-inositol-1,2,6-trisphosphate were synthesized in good yield:
D-3,4,5-tri-O-(2-acetoxy)benzoyl carbamoyl-1,2,6-trisphosphate
D-3,4,5-tri-O-butylcarbamoyl-1,2,6-trisphosphate
D-3,4,5-tri-O-methylcarbamoyl-1,2,6-trisphosphate

EXAMPLE 7

Injection of carrageenan into the subplanar surface of the rat hind-paw induces tissue damage and an inflammatory reaction that results in pronounced oedema. The degree of oedema can be reproducibly quantified by measuring paw circumference.

Two groups of five male rats were injected 2 hours and 1 hour before injection of carrageenan with 80 mg/kg D-3,4,5-tri-O-hexanoyl-myo-inositol-1,2,6-trisphosphate (PP 10-202) or Krebs ringer solution (control) respectively.

Measurement of the paw diameter was made at specific intervals.

The results show that an injection of PP 10-202 reduces the oedema by 41% one hour after the induction of the damage as compared to control. Two and a half hour after the induction of the damage the oedema was reduced by 49% compared to control. Thus, the inflammation in the animals treated with PP 10-202 was strongly reduced and the duration of the counteractive effect was prolonged.

EXAMPLE 8

In an experiment similar to the procedure described in example 7 the antiinflammatory effect D-3,4,5-tri-O-isobutyryl-myo-inositol-1,2,6-trisphosphate (PP10-201) was determined. The results are summarized in the following table:

|  | Reduction of inflammation | |
| --- | --- | --- |
|  | after one hour | after three hour |
| Control | 0% | 0% |
| Administration of PP10-201 | 49% | 57% |

The results show that the administration of PP10-201 strongly reduces the inflammation with a long duration.

We claim:

1. A method of preventing, alleviating or combatting vascular leakage or oedema formation in an animal comprising administering to an animal in need thereof an ester of inositoltriphosphate in an amount effective to prevent, alleviate, or combat vascular leakage or oedema formation, said ester having at least one esterified inositol hydroxy group and said ester optionally being present as a salt.

2. A method according to claim 1, wherein the tissue damage is a vascular leakage.

3. A method according to claim 2, wherein the vascular leakage is an extravasation and/or an oedema.

4. A method according to claim 1, wherein said ester of inositoltrisphosphate is an ester of myo-inositoltrisphosphate.

5. A method according to claim 4, wherein said ester of myo-inositoltrisphosphate is an ester of D-myo-inositol-1,2,6-trisphosphate.

6. A method according to claim 4, wherein said ester of D-myo-inositol-1,2,6-trisphosphate is selected from the group consisting of
   i) D-3,4,5-tri-O-(4-acetoxy)butyryl-myo-inositol-1,2,6-trisphosphate,
   ii) D-3,4,5-tri-O-propionyl-myo-inositol-1,2,6-trisphosphate,
   iii) D-3,4,5-tri-O-butyryl-myo-inositol-1,2,6-trisphosphate,
   iv) D-3,4,5-tri-O-isobutyryl-myo-inositol-1,2,6-trisphosphate,
   v) D-3,4,5-tri-O-(4-hydroxy)pentanoyl-myo-inositol-1,2,6-trisphosphate,
   vi) D-3,4,5-tri-O-dodecanoyl-myo-inositol-1,2,6-trisphosphate,
   vii) D-3,4,5-tri-O-hexanoyl-myo-inositol-1,2,6-trisphosphate,
   viii) D-3,4,5-tri-O-phenylcarbamoyl-myo-inositol-1,2,6-trisphosphate,
   ix) D-3,4,5-tri-O-(2-acteoxy)benzoylcarbamoyl-myo-inositol-1,2,6-trisphosphate,
   x) D-3,4,5-tri-O-butylcarbamoyl-myo-inositol-1,2,6-trisphosphate, and
   xi) D-3,4,5-tri-O-methylcarbamoyl-myo-inositol-1,2,6-trisphosphate.

7. A method according to claim 6, wherein said salt of said ester of inositoltrisphosphate is a salt of sodium, calcium, zinc or magnesium or a mixture of two or more thereof.

8. A method in accordance with claim 1 wherein said ester inositoltrisphosphate is administered in a unit dosage form.

9. A method in accordance with claim 8 wherein said unit dosage is provided in the form of tablets, granules, capsules, solutions or suspensions.

10. The method according to claim 1 wherein the animal is a human.

11. The method according to claim 1 wherein the ester of inositoltrisphosphate has the formula

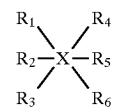

where $R_1$, $R_2$ and $R_3$ are vicinal and all are

where each A may be the same or different and is
   (1) straight or branched chain unsubstituted or substituted alkyl containing 1 to 24 carbon atoms
   (2) unsubstituted or substituted cycloalkyl containing 3 to 16 carbon atoms
   (3) unsubstituted or substituted alkenyl containing 2 to 24 carbon atoms
   (4) unsubstituted or substituted cycloalkenyl containing 5 to 16 carbon atoms
   (5) unsubstituted or substituted aryl containing 6 to 24 carbon atoms
   (6) unsubstituted or substituted aralkyl containing 7 to 48 carbon atoms (7) unsubstituted or substituted alkaryl containing 7 to 48 carbon atoms (8) unsubstituted or substituted aralkenyl containing 8 to 48 carbon atoms (9) unsubstituted or substituted alkenylaryl containing 8 to 48 carbon atoms

(10) a heterocyclic ring said heterocyclic being

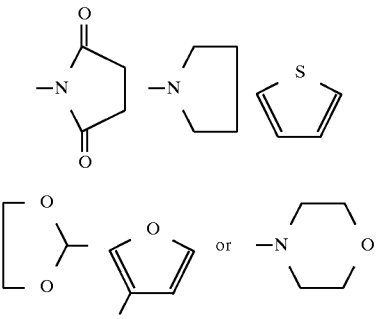

said meaning (1) to (10) being unsubstituted or substituted with hydroxy, oxo, alkoxy, aryloxy, halo, cyano, isocyano, carboxy, esterified carboxy, amino, substituted amino, formyl, acyl, acyloxy, acylamino, sulfinyl, sulfonyl, phosphine, phosphinyl, phosphonyl, mercapto, alkylthio, arylthio, silyl, silyloxy, silylthio, nitro or azido

(11) carboxy

(12) esterified carboxy

(13) amino or

(14) substituted amino where $R_4$, $R_5$ and $R_6$ are vicinal and all are

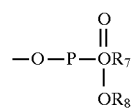

where $R_7$ and $R_8$ are the same or different and are (1) hydrogen or (2) mono-, di- or trivalent cation and where X is a radical of myo-inositol or a configuration isomer thereof.

12. The method according to claim 11 wherein $R_1$, $R_2$ and $R_3$ are the same.

13. The method according to claim 11 wherein $R_1$, $R_2$ and $R_3$ are independently (1)

where n is an integer between 1 and 10;

(2)

where n is an integer between 1 and 10 and where $R_9$ is a substituted or unsubstituted straight or branched alkyl, cycloalkyl, aryl or alkaryl;

(3)

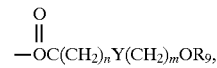

where n and m is an integer between 1 and 10 and where Y is oxygen or sulphur;

(4)

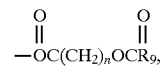

where n and m is an integer between 1 and 10, where Y is oxygen or sulphur and where $R_9$ is a substituted or unsubstituted straight or branched alkyl, cycloalkyl, aryl or alkaryl;

(5)

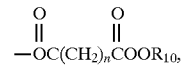

where n is an integer between 1 and 10 and where $R_9$ is a substituted or unsubstituted straight or branched alkyl, cycloalkyl, aryl or aralkyl;

(6)

where n is an integer between 1 and 10 and where $R_{10}$ is hydrogen or a substituted or unsubstituted straight or branched alkyl, cycloalkyl, aryl or aralkyl;

(7)

where n is an integer between 1 and 10 and where $R_9$ is a substituted or unsubstituted straight or branched alkyl, cycloalkyl, aryl or aralkyl;

(8)

where n is an integer between 1 and 10 and where $R_9$ is a substituted or unsubstituted straight or branched alkyl, cycloalkyl, aryl or aralkyl, and where $R_{10}$ is hydrogen or substituted or unsubstituted straight or branched alkyl, cycloalkyl, aryl or aralkyl;

(9)

—OC(CH$_2$)$_n$NR$_{10}$COR$_9$, where n is an integer between 1 and 10 and where $R_9$ is a substituted or unsubstituted, straight or branched alkyl, cycloalkyl, aryl or aralkyl and where $R_{10}$ is hydrogen or substituted or unsubstituted straight or branched alkyl, cycloalkyl, aryl or aralkyl;

(10)

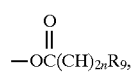

where n is an integer between 1 and 10 and where $R_9$ is a substituted or unsubstituted straight or branched alkyl, cycloalkyl, aryl or aralkyl;

(11)

where $Z^1$ is substituted or unsubstituted cycloalkyl;

(12)

where $Z^1$ is substituted or unsubstituted cycloalkyl and where n is an integer between 1 and 10;

(13)

where $Z^2$ is substituted or unsubstituted phenyl, biphenyl, naphthyl, anthracenyl or phenantrenyl;

(14)

where $Z^3$ us substituted or unsubstituted heterocyclic selected from the group consisting of

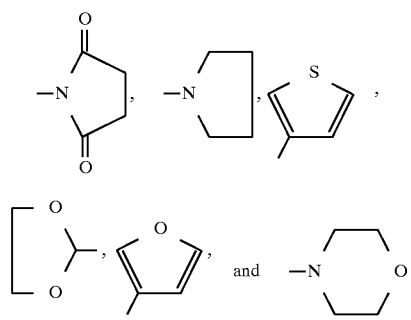

(15)

where $Z^3$ is substituted or unsubstituted heterocyclic compound selected from the group consisting of

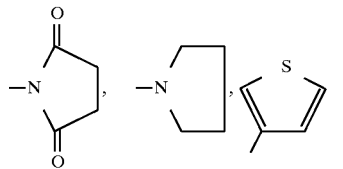

(16)

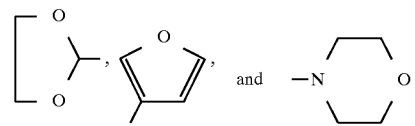

where n and m is an integer between 1 and 10, where $R_9$ is a substituted or unsubstituted straight or branched alkyl, cycloalkyl, aryl, alkaryl and where $R_{10}$ and $R_{11}$ are independently hydrogen or substituted or unsubstituted straight or branched alkyl, cycloalkyl, aryl, alkaryl;

(17) -O-acetyl, -O-propionyl, -O-butyryl, -O-isobutyryl, -O-(4-acetoxy)butyryl, -O-valeryl, -O-isovaleryl, -O-(4-propionyloxy)valeryl, -O-pivaloyl, -O-hexanoyl, -O-octanoyl, -O-decanoyl, -O-dodecanoyl, -O-tetradecanoyl, -O-hexadecanoyl or -O-octadecanoyl,

(18) -O-methylcarbamoyl, -O-ethylcarbamoyl, -O-propylcarbamoyl, -O-butylcarbamoyl, -O-phenylcarbamoyl, -O-benzoylcarbamoyl, -O-(2-acetoxy)benzoylcarbamoyl, -O-(2-propionyloxy) benzoylcarbamoyl or chlorosulfonylcarbamoyl.

14. The method according to claim 11 wherein X is myoinositol, cisinositol, epiinositol, alloinositol, neoinositol, mucoinositol, chiroinositol, or scylloinositol.

15. The method according to claim 11 wherein $R_1$, $R_2$ and $R_3$ are the same.

16. The method according to claim 11 wherein $R_1$, $R_2$ and $R_3$ are the same and are

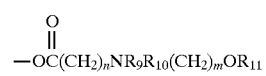

and n is 2–4 and $R_9$ is methyl, ethyl or propyl.

17. The method according to claim 11 wherein $R_1$, $R_2$ and $R_3$ are

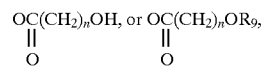

wherein n is 1, m is 2–4, and $R_9$ is methyl, ethyl or propyl.

18. The method according to claim 11 wherein $R_1$, $R_2$ and $R_3$ are

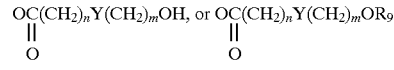

wherein $R_9$ is methyl, ethyl or propyl and n is 1 or 2.

19. The method according to claim 11 wherein $R_1$, $R_2$ and $R_3$ are

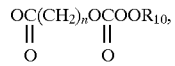

wherein n is 2 or 3 and $R_{10}$ is H, methyl, ethyl or propyl.

20. The method according to claim 11 wherein $R_1$, $R_2$ and $R_3$ are the same and are

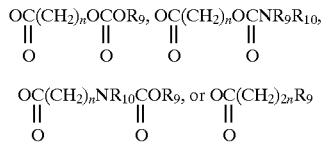

wherein n is 1, $R_9$ is methyl, ethyl or propyl and $R_{10}$ is hydrogen.

21. The method according to claim 11, wherein $R_1$, $R_2$ and $R_3$ are the same and are

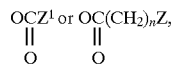

wherein Z is $CH(CH)_2$, $CH(CH_2)_3$, $CH(CH_2)_4$, $CH(CH_2)_5$, $CH(CH_2)_6$, or $CH(CH_2)_2CH_2$, and n is 1.

22. The method according to claim 11 wherein $R_1$, $R_2$ and $R_3$ are

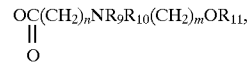

wherein n is 1 or 2, m is 2 or 3, $R_9$ is methyl, ethyl or propyl and $R_{10}$ and $R_{11}$ are hydrogen.

23. The method according to claim 11 wherein the inositoltrisphosphate is

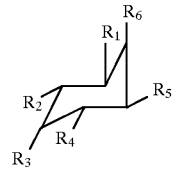

24. A method of preventing, alleviating or combating tissue damage resulting from vascular leakage or oedema formation in an animal comprising administering to an animal in need thereof an ester of inositol triphosphate in an amount effective to prevent, alleviate or combat vascular leakage or oedema formation, said ester having at least one inositol hydroxy group esterified, and optionally being present as a salt.

* * * * *

UNITED STATES PATENT AND TRADEMARK OFFICE
CERTIFICATE OF CORRECTION

PATENT NO.   : 5,866,557
DATED        : February 2, 1999
INVENTOR(S)  : Lars Persson et al.

It is certified that error appears in the above-identified patent and that said Letters Patent is hereby corrected as shown below:

Title page,
Item [57] ABSTRACT, delete entire ABSTRACT, and insert -- The use of an ester of inositoltrisphosphate for the preparing of a medicament for preventing, alleviating or combatting inflammatory conditions in mammals including man. --

Column 1,
Line 5, after the title, insert -- The present invention relates to the use of an ester of inositoltrisphosphate for the preparation of a medicament for preventing, alleviating or combatting inflammatory conditions in mammals including man.
  Injury or destruction of tissue should be understood as damage to an aggregation of specialized cells with a particular function both internally and externally in the body, such as different organs or parts of these, vessels, skin etc.
  Tissue damage involves a complex series of events such as dilation of vessel walls e.g. arterioles, capillaries and venules, increased permeability of fluids including e.g. plasma proteins and increased blood flow. Increased vascular leakage often results in extravasation and oedema formation which characterize the damage of different tissues.
  Often tissue damage and inflammatory conditions are characterized by signs of pain, heat, redness, swelling and loss of function.
  Tissue damage is not defined as a disease per se but is often a component in different diseases of both acute or chronic nature. --

Column 2,
Line 42, "substantialy" should read -- substantially --

Column 5,
Line 39, "unsubstituted such as" should read -- unsubstituted cycloalkly such as --

Column 7,
Line 23, "branced" should read -- branched --
Line 43, "esterfield" should read -- esterified --
Line 50, "OR7" should read -- OR --

UNITED STATES PATENT AND TRADEMARK OFFICE
CERTIFICATE OF CORRECTION

PATENT NO. : 5,866,557
DATED : February 2, 1999
INVENTOR(S) : Lars Persson et al.

It is certified that error appears in the above-identified patent and that said Letters Patent is hereby corrected as shown below:

Column 9, claim 1,
Line 57, inositoltriphosphate" should read -- inositoltrisphosphate --

Column 10, claim 6,
Line 24, "acteoxy" should read -- acetoxy --

Column 11, claim 13,
Line 1, "$-OC(CH_2)_n OH$" should read $-O-C-(CH_2)_n-OH-$

Line 2, "$-OC(CH_2)_n OR_9$" should read $-O-C-(CH_2)_n OR_9$ --

Column 12, claim 13,
Line 3, "$-OC(CH_2)_n Y(CH_2)_m OH$" should read $-O-C-(CH_2)_n Y-(CH_2)_m OH-$ Line 4, "$-OC(CH_2)_n Y(CH_2)_m OR_9$" should read $-O-C-(CH_2)_n Y-(CH_2)_m OR_9-$ Line 5, "$-OC(CH_2)_n OCR_9$" should read $-O-C-(CH_2)_n O-C-R_9-$ Line 6, "$-OC(CH_2)_n COOR_{10}$" should read $-O-C-(CH_2)_n C-OR_{10}$ --

Column 13, claim 13,
Line 10, "$-OC(CH)_{2n} R_9$" should read $-O-C-(CH_2)_n -R_9$ --

UNITED STATES PATENT AND TRADEMARK OFFICE
CERTIFICATE OF CORRECTION

PATENT NO. : 5,866,557
DATED : February 2, 1999
INVENTOR(S) : Lars Persson et al.

It is certified that error appears in the above-identified patent and that said Letters Patent is hereby corrected as shown below:

Column 13, claim 14,
"us" should read -- is --

Column 15, claim 19,
Line 1, "$OCOOR_{10}$" should read -- $COOR_{10}$ --
         $\|$
         $O$ Column 16, claim 23,
Line 15, insert a period after compound.

Signed and Sealed this

Fifth Day of February, 2002

Attest:

JAMES E. ROGAN
Attesting Officer    Director of the United States Patent and Trademark Office